(12) United States Patent
Baluta (10) Patent No.: US 8,346,698 B2
(45) Date of Patent: Jan. 1, 2013

(54) SYSTEM AND METHOD FOR OPTIMIZING DEVELOPMENT, IMPLEMENTATION AND MANAGEMENT OF ORDERS

(75) Inventor: Wasyl Baluta, Calgary (CA)

(73) Assignee: Wairever, Inc., Calgary, Ontario (CA)

( * ) Notice: Subject to any disclaimer, the term of this patent is extended or adjusted under 35 U.S.C. 154(b) by 736 days.

(21) Appl. No.: 12/417,094

(22) Filed: Apr. 2, 2009

(65) Prior Publication Data

US 2009/0254509 A1 Oct. 8, 2009

Related U.S. Application Data

(60) Provisional application No. 61/042,582, filed on Apr. 4, 2008.

(51) Int. Cl.
*G06F 17/00* (2006.01)
*G06F 7/00* (2006.01)

(52) U.S. Cl. .......................... 706/45; 707/705

(58) Field of Classification Search ................. None
See application file for complete search history.

(56) References Cited

U.S. PATENT DOCUMENTS

| | | | |
|---|---|---|---|
| 5,740,800 | A | 4/1998 | Hendrickson et al. |
| 6,983,423 | B2 | 1/2006 | Dvorak et al. |
| 7,230,529 | B2 | 6/2007 | Ketcherside, Jr. et al. |
| 7,359,922 | B2 | 4/2008 | Young-Lai et al. |
| 7,672,987 | B2 * | 3/2010 | Mukherjee et al. ........... 707/776 |
| 7,822,626 | B2 | 10/2010 | Harp et al. |
| 2003/0074220 | A1 | 4/2003 | Brandt |
| 2004/0078231 | A1 | 4/2004 | Wilkes et al. |
| 2004/0122661 | A1 | 6/2004 | Hawkinson et al. |
| 2005/0060191 | A1 | 3/2005 | Parkins et al. |
| 2007/0005154 | A1 | 1/2007 | Lancaster et al. |
| 2007/0005394 | A1 | 1/2007 | Bleyendaal et al. |
| 2007/0198293 | A1 | 8/2007 | Ash et al. |
| 2007/0198294 | A1 | 8/2007 | Ash et al. |
| 2007/0203746 | A1 | 8/2007 | DeHaan et al. |
| 2008/0177579 | A1 | 7/2008 | DeHaan |

OTHER PUBLICATIONS

Krauthammer, et al. "Term identification in the biomedical literature," Journal of BioMedical Informatics, vol. 37, Issue 6, Dec. 2004, pp. 512-526.
Cooper, G., et al., "An Experiment Comparing Lexical and Statistical Methods for Extracting MeSH Terms From Clinical Free Text," J Am Med Inform Assoc. 1998; pp. 62-75.
Nadkarni, P., et al., "UMLS Concept Indexing for Production Databases", a feasibility study. J. Am Med Inform Assoc. 2001: pp. 80-91.
Zou Q., Chu, et al., "IndexFinder: A Method of Extracting Key Concepts From Clinical Tests for Indexing," Proc. AMIA Symp. 2003; 763-7.
Ruch, P., et al. "MEDTAG: Tag-like Semantics for Medical Document Indexing," 1999 AMIA, Inc., pp. 137-141.

* cited by examiner

*Primary Examiner* — Alan Chen
(74) *Attorney, Agent, or Firm* — Dinsmore & Shohl LLP (57) ABSTRACT

A system and method is provided for developing, implementing and managing orders whereby a raw order set can be resolved into a canonical order set to identify at least one order within the one raw order set. A commonality analysis can be performed by comparing one canonical order set with another canonical order set to determine at least one common order subset. The canonical order sets sharing at least one common order subset can then be restructured into a hierarchical structure, and prioritized to minimize downstream processing.

32 Claims, 9 Drawing Sheets

SYSTEM AND METHOD FOR OPTIMIZING DEVELOPMENT, IMPLEMENTATION AND MANAGEMENT OF ORDERS

CROSS REFERENCE TO RELATED APPLICATIONS

This application claims the priority of U.S. Provisional Patent Application No. 61/042,582 filed Apr. 4, 2008, which is incorporated by reference in this specification.

TECHNICAL FIELD

The present disclosure is related to the field of artificial intelligence-based systems and methods for developing, implementing and managing orders and order inventories and, in particular, designing and validating clinical orders and order inventories including medications/pharmaceuticals, clinical interventions such as laboratory tests and procedures, diagnostic imaging tests and procedures, and treatment protocols.

BACKGROUND

In treating a patient, physicians, nurses or clinical specialists (collectively "clinicians") may order an intervention for the patient, including diagnostic tests, or treatment protocols for the patient or a combination of both, or to track the execution/performance of the delivery of such orders. In making such clinical orders for the encounter, the clinician will typically provide the order or set of orders through a Computerized Provider Order Entry ("CPOE") system, or an Electronic Medical Records ("EMR") system. The difficulty with such methods is that the inventory of these systems must contain all orders and sets of orders that may be possible to be ordered during the delivery of care, or alternatively allow for free-form entry. Practically speaking, this can represent an inventory of 10,000-100,000 possible individual orders. In constructing this inventory for predefined standardized inventories, or reconciling against a standard nomenclature with models using free-form orders, the clinical orders are usually defined by the physician using natural language and using terminology that, while being familiar to the physician, may not be in standardized form or vernacular. As such, the diagnostic and treatment orders may be described numerous different ways. If the protocol is being entered into a CPOE or EMR system, then there is the possibility that errors could be introduced into the CPOE or EMR inventory given that the natural language orders prepared by the clinicians may be incorrectly interpreted, duplicated, and/or incorrectly configured into the system.

It is, therefore, desirable to provide a system and method for developing, implementing and managing orders, such as clinician orders, for the purpose of developing a standardized order inventory.

SUMMARY

In one embodiment of the system and method described herein, medical investigations and treatment processes can involve a physician or clinical specialist in "ordering" something for a patient. These "orders" can be one orderable item (or simply "order"), or several orderable items processed as an "order set".

The order sets can typically be in some electronic document form using free form English names and descriptions for orders. These documents are called "raw" order set documents. In a health care system, approved or supported orders can form a sort of inventory of items called an "authoritative catalogue". The catalogue can be the authoritative list from which clinicians or specialists can select or recommend an orderable item to be applied in a clinical situation with a patient.

Medical research and practice is very active and very diverse with new developments constantly being created. As new research unfolds and as new clinical techniques are developed, the "approved" or "recommended" orderable items, order sets and procedures in the catalogue can change, grow or become invalid over time.

In one embodiment, a system and method can be provided in the form of an application for validating order set documents against an authoritative catalogue of a health authority. Every order set document created by a clinical specialist, researcher, physician, etc. can be reconciled against a catalogue to ensure that the order set is using only orderable items defined in the catalogue. If an orderable item referred to in an order set document is not in the catalogue, then the item may not necessarily be available. The method of validation can help ensure that a health authority's medical and clinical processes are supported, safe and accessible.

In another embodiment, the method can be embodied in a computer software application that facilitates the development, implementation and management of standardized order sets. The application can further facilitate organization, validation, translation, minimization and prioritization of order sets during the implementation and ongoing maintenance of a CPOE or EMR system.

In another embodiment, the system and method can simplify the effective organization of order sets. The method can treat them as contextualized orders for specific limited purpose produced and managed by clinicians with appropriate skill. The order sets can become collections of other order sets and individual orders that can be used over and over. In doing so, the system and method can centralize the management of order sets and protect them through a secure access to the order sets.

In another embodiment, the system and method can interpret natural language orders and understand synonyms. The system and method can further recognize spelling errors and can implicitly handle paraphrases. In addition, the system and method can handle alternative names used in various environments, find canonical order items or variant order items, find context of orders, retain structure of order sets as defined and let analysts confirm automated interpretation of orders through a self-validating process and can complete searches completely and efficiently through artificial intelligence assisted matching. This matching of an item to a canonical item of an authoritative catalog is called canonical matching, and the canonical item is also known as a canonical order or canonical item. In so doing, hours of manual searching and matching for canonical items can be reduced to minutes and can provide matches with improved confidence.

In another embodiment, the system and method can improve matching and improve confidence in match results. Many searches can be applied simultaneously with explanations as to how results were found. In addition, the searches can show the best results and nearest alternate results. The system and method can search sources in their entirety and can score the search results. In a representative embodiment, the system and method can automatically match most orders in the top five search results, with a very high accuracy for medication, lab, and diagnostic orders.

In another embodiment, the system and method can find similarities in order sets and can identify common items between order sets. A canonical order set is an order set in which at least one order item has been matched to a canonical order item from an authoritative catalogue. In further embodiments, the system and method can find the most similar order sets and can find the most popular orders. In so doing, the system and method can support structured design of order set content, can minimize unique order subgroups, and maximize reuse of order subgroups.

In another embodiment, the system and method can provide top-down goal-oriented management of order set development, validation, and deployment and can find status in organizational master catalogues, departmental catalogues, various development stage catalogues, and industry standard medical catalogues and nomenclatures. Each of these examples can be considered to be an "authoritative catalogue". The system and method can further identify items that are complete and items that are incomplete and provide status reports that can identify the incomplete orders and from which catalogues the incomplete orders came from.

Broadly stated, a method is provided for implementing raw order sets containing at least one order, the method comprising the steps of: resolving the at least one raw order set into at least one canonical order set to identify the at least one order within the at least one raw order set; and performing a commonality analysis by comparing the least one canonical order set with at least one other canonical order set to determine at least one common order subset.

Broadly stated, a method is provided for implementing raw orders containing at least one order item, the method comprising the steps of: receiving a raw order comprising at least one order item and resolving the at least one order item to a canonical item of an authoritative catalogue of order items, with either canonical or variant forms of order items, to produce a canonical order set; performing a commonality analysis on the canonical order set by comparing the canonical order set to other canonical order sets and organizing the canonical order set into a hierarchical structure or a prioritized order; validating the at least one order item in the canonical order set to produce a validated order set; configuring and testing the validated order set; and activating the validated order set.

Broadly stated, a system is provided for implementing raw order sets containing at least one order, comprising: means for resolving the at least one raw order set into at least one canonical order set to identify the at least one order within the at least one raw order set; and means for performing a commonality analysis by comparing the one canonical order set with at least one other canonical order set to determine at least one common order subset.

Broadly stated, a system is provided for implementing raw orders containing at least one order item, comprising: means for receiving a raw order comprising at least one order item and resolving the at least one order item to a canonical item of an authoritative catalogue of order items, with either canonical or variant forms of order items, to produce a canonical order set; means for performing a commonality analysis on the canonical order set by comparing the canonical order set to other canonical order sets and organizing the canonical order set into a hierarchical structure or a prioritized order; means for validating the at least one order item in the canonical order set to produce a validated order set; means for configuring and testing the validated order set; and means for activating the validated order set.

Broadly stated, a method is provided implementing raw order sets containing at least one order, the method being embodied on a computer-readable medium such that, when implemented on a general purpose computing platform, the method permits the implementation of a raw order set containing at least one order, the computer-readable medium comprising: a software code segment that resolves the at least one raw order set into at least one canonical order set to identify the at least one order within the at least one raw order set; and a software code segment that performs a commonality analysis by comparing the one canonical order set with at least one other canonical order set to determine at least one common order subset.

Broadly stated, a method is provided for implementing raw orders containing at least one order item, the method being embodied on a computer-readable medium such that, when implemented on a general purpose computing platform, the method permits the implementation of raw orders containing at least one order item, the computer-readable medium comprising: a software code segment that receives a raw order comprising at least one order item and resolving the at least one order item to a canonical item of an authoritative catalogue of order items, with either canonical or variant forms of order items, to produce a canonical order set; a software code segment that performs a commonality analysis on the canonical order set by comparing the canonical order set to other canonical order sets and organizing the canonical order set into a hierarchical structure or a prioritized order.

DETAILED DESCRIPTION OF EMBODIMENTS

In one embodiment, a system and method for developing, implementing, and managing orders is provided. In another embodiment, a system and method for developing, implementing, and managing orders in an electronic health records environment is provided. For the clinical standardization and configuration of CPOE and EMR, natural language order sets can be submitted by clinicians (physicians, lab specialists, diagnostic imaging specialists, nurses, pharmacists, etc.) to establish a standardized inventory catalogue of orders as well as orders sets for the system. Development and implementation of orders and order sets involves creating consistent, well-structured, clinically valid, standardized clinical order sets from unchecked raw order sets provided by clinicians.

Figure 1:
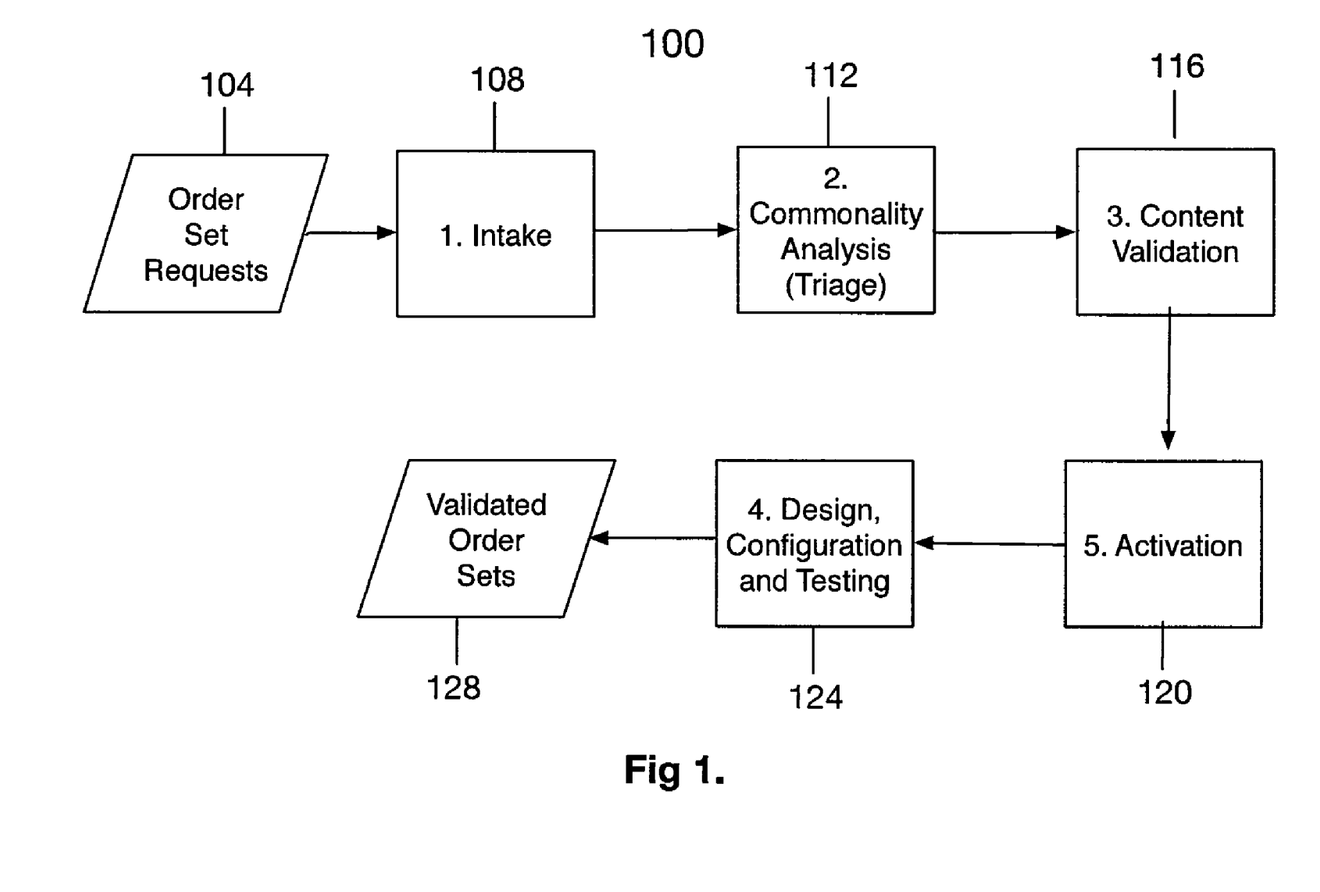
FIG. 1 is a flowchart depicting an order set management process.

Referring to FIG. 1, a flowchart of order set implementation and management process 100 is shown using one embodiment of the system and method for clinician orders through a Clinical Order Set Standards Management System ("COSSM"), also known as the Plexina™ process. The Plexina process, in one embodiment, can include five major functions or steps in developing and managing clinical order sets: (i) Intake, step 108; (ii) Commonality Analysis, step 112; (iii) Content Validation, step 116; (iv) Design, Configuration and Testing, step 120; and (v) Activation, step 124. In this embodiment, an Order Set Request to develop, validate, and implement a clinician's orders is initiated at step 104. The order set is received at Intake step 108 and follows the sequential steps of order set implementation and management process 100. At step 112, a Commonality Analysis is performed to determine the common elements of the clinician's orders. At step 116, the content of the clinician's order is validated. At step 120, the design, configuration and testing of an order set is carried out. At step 124, the order set is activated in process 100. At step 128, validated order sets are made available for use in the development, implementation and management of future clinician orders.

Figure 2:
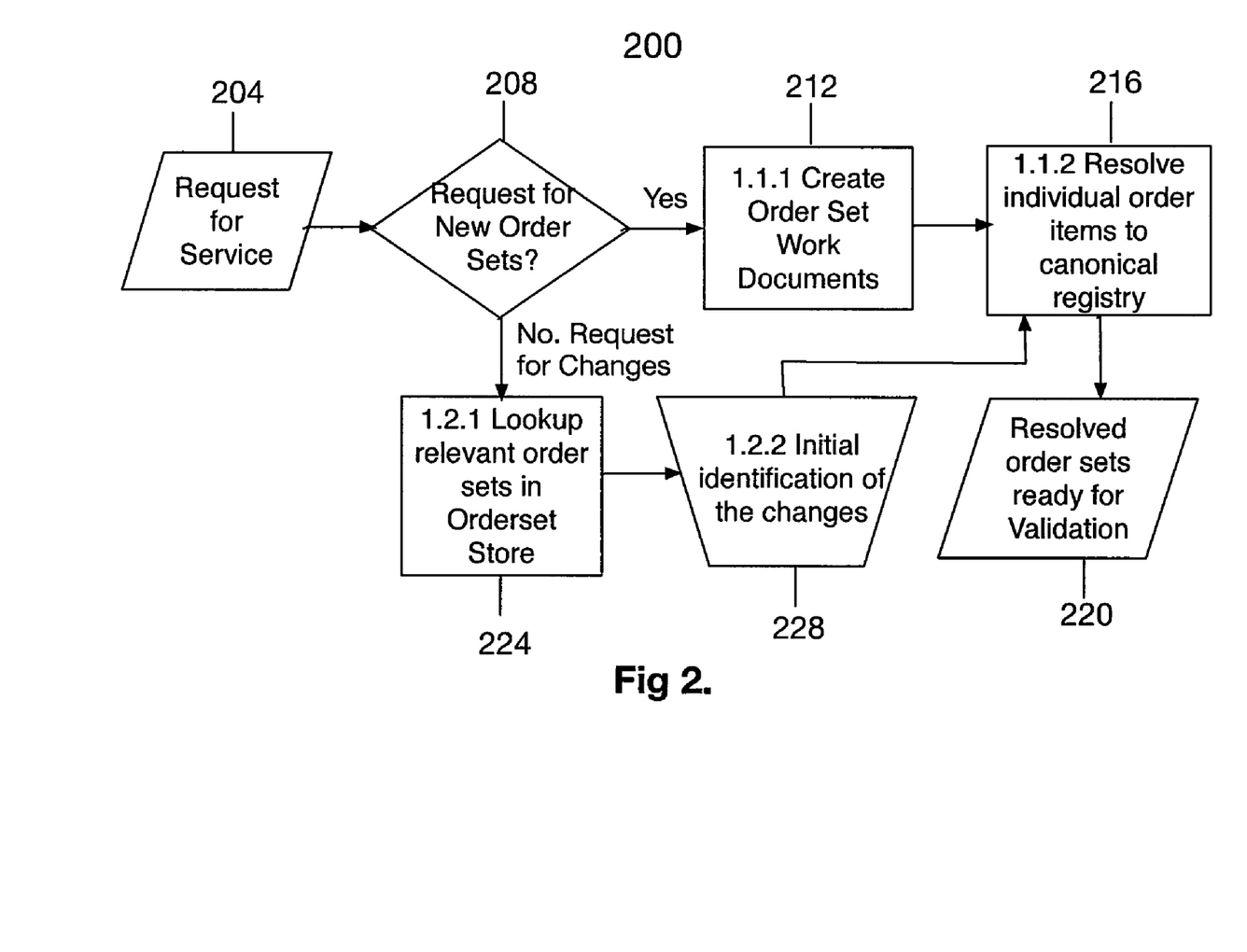
FIG. 2 is a flowchart depicting the Intake step of the process of FIG. 1.

Referring to FIG. 2, a flowchart depicting Intake process 200 of order set requests is shown, and is a detailed view of the internal steps of step 108 of FIG. 1. Clinicians define order sets for care delivery to address clinical situations. The clinicians can request creation of new order sets or request changes to the existing ones. A request can include natural text description of "raw orders" for an order set in hand written documents, and a variety of basic electronic documents such as free-form text, optical character recognized ("OCR") output, word-processor documents, spreadsheet documents and tabular forms, etc. In the embodiment depicted in FIG. 2, the request for service is made at step 204. At step 208, Intake process 200 inquires whether the request is for a new order set. If "yes", Intake process 200 can create a new Order Set Work Document at step 212 for every request for a new order set, and can identify each individual order item requested by the clinician for the newly created order set. If "no", such that a request that results in changes to existing order sets, Intake process 200 can look up known relevant order sets from an inventory of known order sets or an "Order Set Store" at step 224, and at step 228, Intake process 200 can identify the particular order items in the documents that are relevant to the changes. In one embodiment, step 228 can be performed by using automated techniques, as well known to those skilled in at the art. In embodiments concerning clinician orders, step 228 can further comprise the step of manually verifying the order items to ensure a desired level of accuracy is achieved when the system and method is used in a health care environment.

At step 216, Intake process 200 can use common natural language techniques to automatically match or tag each order item in Order Set Work Documents produced at step 212 or changes made to existing order sets produced at step 228 against the best most-likely matched item in the order inventory catalogue (master or departmental), or a standard nomenclature, or a clinical coding standard such as those published by:

Systematized Nomenclature of Medicine—Clinical Terms ("SNOMED CT");
Unified Medical Language System ("UMLS");
International Statistical Classification of Diseases and Related Health Problems ("ICD-9", "ICD-10");
Logical Observation Identifiers Names and Codes ("LOINC"); and
Digital Imaging and Communication in Medicine ("DICOM").

This process of matching or tagging an order item is referred to as 'resolving to canonical registry', or 'canonical matching'. In this embodiment, Intake process 200 can resolve a raw order set to a canonical order set, by canonically matching all orders contained within it. Additionally, each order can have additional categories (clinical unit or department) and attributes (dose, form, route, collection time parameters, or special instructions) associated with it. The output of Intake process 200 is a set of canonical order sets ready for validation at step 220.

There are several major challenges with automated natural language matching approaches to identify clinical orders:
   i) no one strategy for identification of an order works best for all types of orders;
   ii) the context of the order in the order set has to be considered;
   iii) the authors and editors can make one or more types of common errors when writing clinical orders; automated error resolution must be handled by the matching algorithm;
   iv) not all terms involved in a clinical order name are relevant for the discrete identification of the order; and
   v) as the order inventory catalogue (dictionary) changes (new items introduced, items removed, or items changed), the matching algorithm must adapt appropriately.

The solution for a matching algorithm that addresses all of these conditions is not obvious and requires significant experimentation to arrive at a suitable and reasonably accurate approach. In other embodiments, manual validation of an item suggested by the matching algorithm may be required to achieve 100% confidence in the result regardless of how accurate the automated matching is, or to select a possible acceptable alternate suggestion. Furthermore, manual validation effort may still be required for other automated or manual process steps such as clinical appropriateness reviews, drug interaction checks, best practice suggestions form design, and so on.

In another embodiment, resolving an order set into a canonical order set can identify the average number of order items in a raw order set. This resolution can also determine how many orders belong to a clinical unit. In further embodiments, this resolution process can be used to identify the average time to validate an order set in addition to being able to estimate the distribution and effort for validation by clinical unit.

Figure 3:
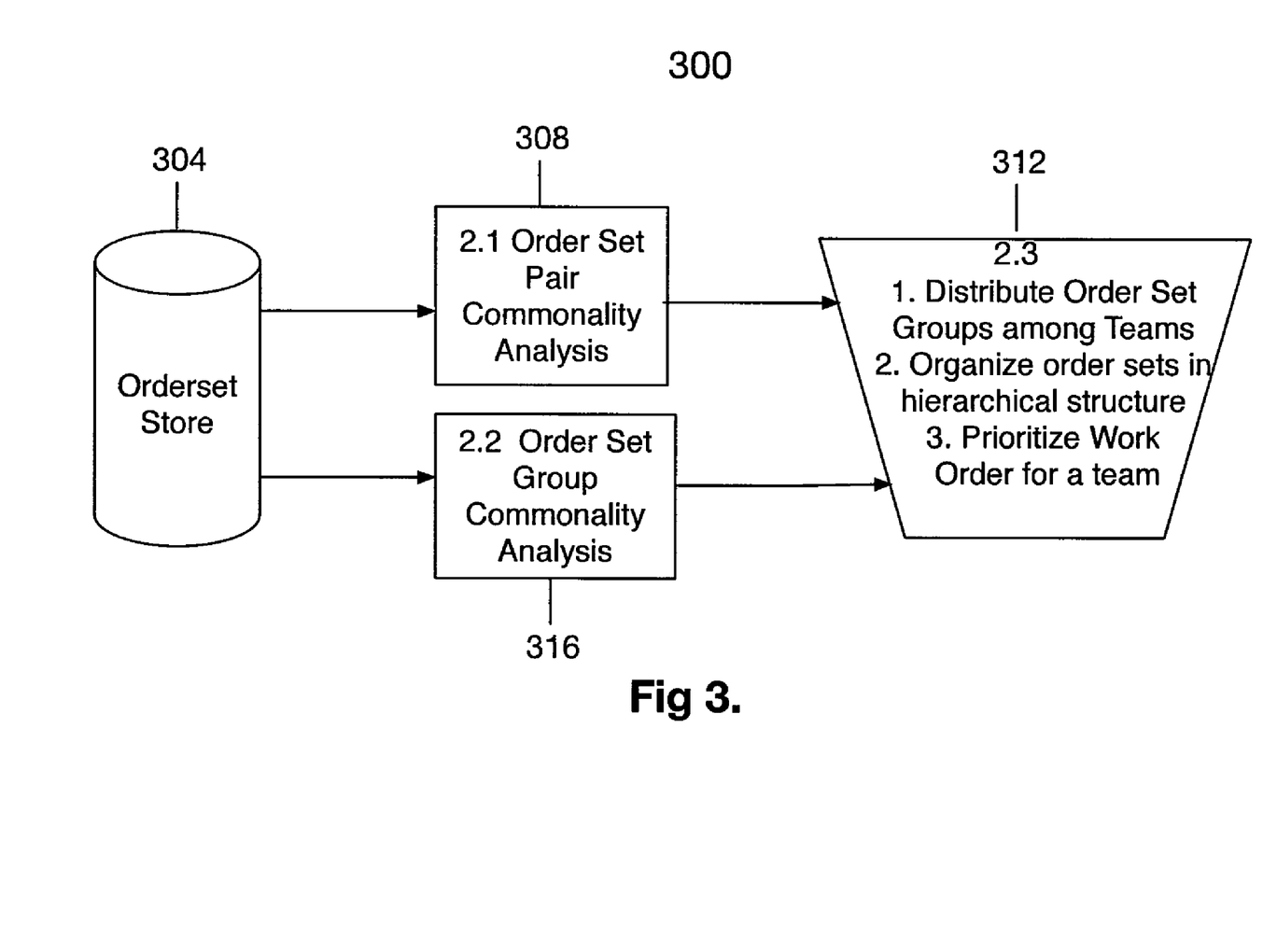
FIG. 3 is a flowchart depicting the Commonality Analysis step of the process of FIG. 1.
Figure 4:
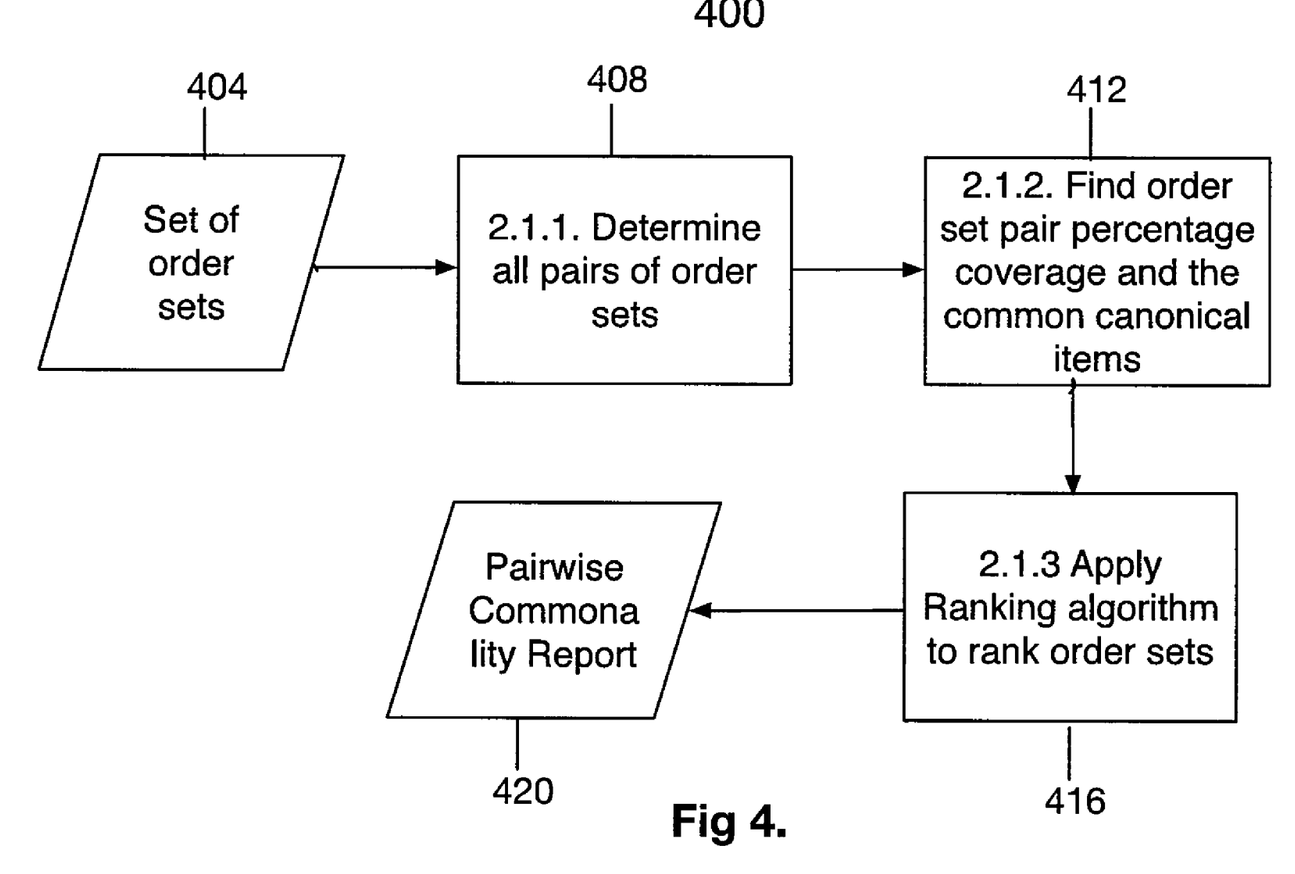
FIG. 4 is a flowchart depicting the Order Set Pair Commonality Analysis step of the process of FIG. 3.
Figure 5:
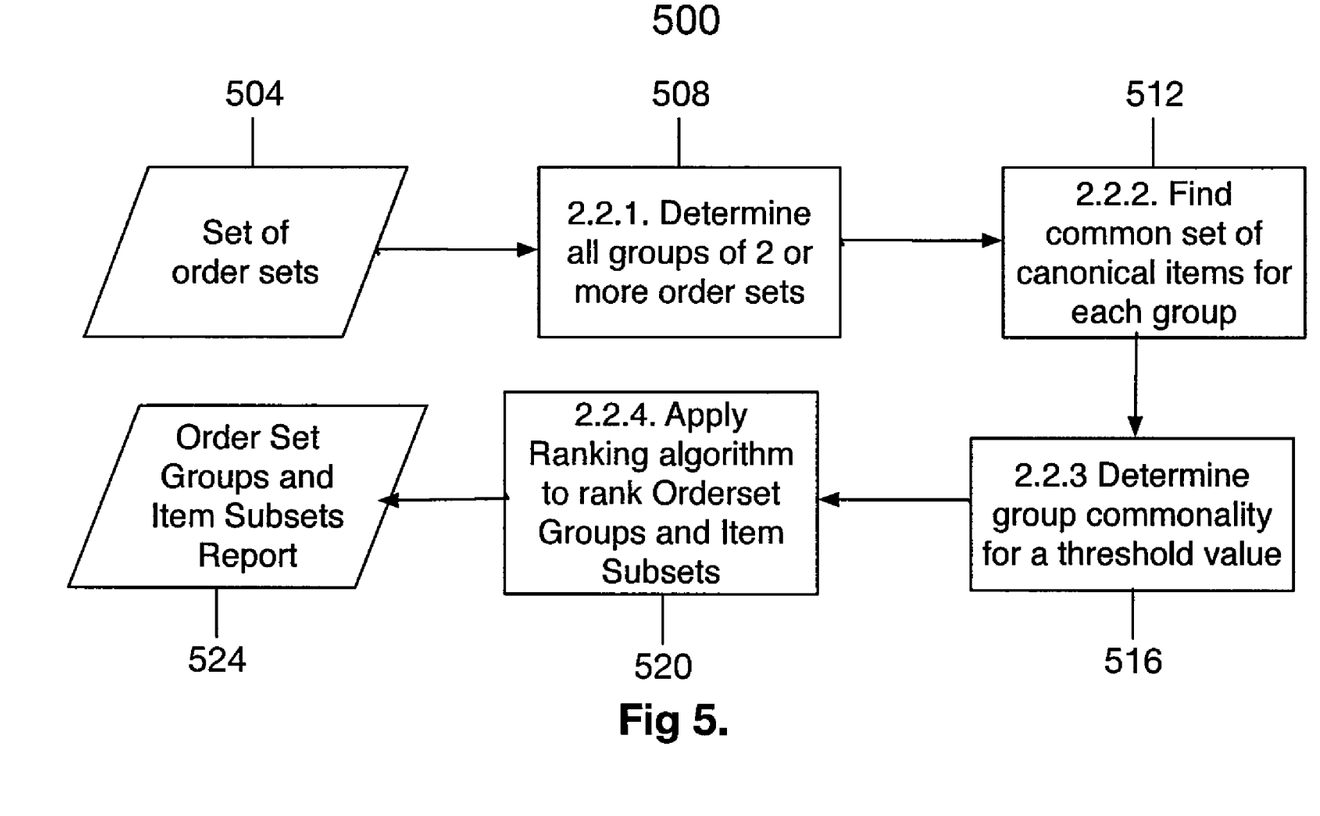
FIG. 5 is a flowchart depicting the Order Set Group Commonality Analysis step of the process of FIG. 3.

Referring to FIG. 3, a flowchart for Commonality Analysis process 300 is shown, a process to assess and triage the development and implementation workload. Commonality Analysis 300 can be a two-step process. Step 308 can analyze commonality between every pair of order sets from an "order set store" provided at step 304 and can generate reports that can guide prioritization of work for a team at step 312. Optionally, the order sets compared can be limited to a subset based on selection parameters. Step 316 can analyze commonality among all groupings of two or more order sets from the order set store as provided at step 304 and can generate reports that can guide workload distribution as well as organization of order sets into a hierarchical structure at step 312. Details of the commonality analysis process in steps 308 and 316 are depicted in FIGS. 4 and 5, and discussed in further detail below.

The input to Commonality Analysis process 300 in FIG. 3 is a set of canonical order sets which themselves are resolved into a set of canonical registry entries. The order sets can be denoted as follows:

Definition: for each $i \in N$, $O_i$ is a unique order set.
Let $\Omega = \{O_i\}$ be the set of all order sets.
Note that in practice, at any given time, $|\Omega|$ is finite. Next, we denote order items in canonical form as follows:

Definition: for each $k \in N$, $c_k$ is a unique canonical order item.
Let $\Theta = \{c_k\}$ be the set of all canonical order items.

Likewise, in practice, at any given time Θ is a finite set.

The Order Set Pair Commonality Analysis process 400 (step 308 of FIG. 3) is shown in FIG. 4. Referring to FIG. 4, all pairs of order sets can be identified, starting at step 408. The set, P, of all order set pairs can be denoted as:

$$P=\{\{O_i,O_j\}|i\neq j\}$$

At step 412, the set of canonical items common between each pair of order sets can be determined by:

$$C(O_i,O_j)=O_i\cap O_j$$

Furthermore, the Percentage Coverage $p_{ij}$ of order set $O_i$ by order set $O_j$ can be determined by:

$$p_{ij}=|C(O_i,O_j)|/|O_i|*100\%$$

Similarly, the Percentage Coverage $p_{ji}$ of order set $O_j$ by order set $O_i$ can be determined by:

$$p_{ji}=|C(O_j,O_i)|/|O_j|*100\%$$

Now the Order Set Pair Commonality, S, can be defined as a set of 4-tuples, where:

$$S=\{(\{O_i,O_j\},C(O_i,O_j),p_{ij},p_{ji})|\{O_i,O_j\}\epsilon P\}$$

At step 416, the order sets can be ranked based on the following factors:
 (i) the number of items an order set has common with other order sets,
 (ii) the total number of order sets it has items common with, and
 (iii) the percentage coverage of other order sets.

The algorithm can allow these factors to be variably weighted. Optionally, process 400 can be limited to consider order set pairings, which meet a minimum threshold based on either number of canonical orders in common, or percentage coverage.

The Group Commonality Analysis process 500 (step 316 in FIG. 3) is shown in FIG. 5. At step 508, all sets of 2 or more order sets can be constructed, referred to as Order Set Groups. The set G of all Order Set Groups can be written as:

$G=\{g|g\epsilon \mathcal{P}(\Omega), |g|\geq 2\}$, where $\mathcal{P}(\Omega)$ is the power set of $\Omega$ When necessary, an Order Set Group can be labelled with subscripts in order to index the order sets.

ex. $g_{2,4,6,7}=\{O_2,O_4,O_6,O_7\}$, where $g_{2,4,6,7}\epsilon G$.

At step 512, for each Order Set Group $g_{k_1, k_2, \ldots, k_m}$, the common set of canonical order items $C(g_{k_1, k_2, \ldots, k_m})$ can be determined, calculated as:

$$C(g_{k_1,k_2,\ldots,k_m})=\cap_{i\epsilon\{1,\ldots,n\}}O_{k_i}$$

At step 516, the size of G can be first reduced. Order Set Groups that are redundant to the commonality analysis process can be removed to form the reduced set G'. An Order Set Group g is considered redundant if there exists another Order Set Group h, where h contains g and the common set of canonical items of g are contained in that of h. Specifically, $$G'=G\setminus\{g\epsilon G|\exists h\epsilon G \ s.t. g\subset h \text{ and } C(g)\subseteq C(h)\}.$$

Next, Order Set Group Commonality R can be computed as:

$$R=\{(g,C(g))|g\epsilon G'\}$$

We can construct subsets of G' subject to a threshold condition where we require groups of order sets to have at least t items in common:

$$R(t)=\{g\epsilon G'||C(g)|\geq t\}$$

At step 520, the Order Set Groups can be ranked based on the following factors:
 (i) the cardinality of each Order Set Group, and
 (ii) the cardinality of the common set of canonical order items that the group contains.

The ranking algorithm allows these factors to be variably weighted.

The reports generated by the system and method through the Commonality Analysis process at steps 308 and 316 in FIG. 3, serve as a basis for the decision making process at step 312 in FIG. 3. Step 312 is discussed below with respect to various embodiments:

In one embodiment, a common order item subsets report generated at step 316 of FIG. 3 can help organize order sets sharing common order subsets into a hierarchical structure.

For example,
If order set $O_1$, is made up of items: $c_1, c_2, c_3, c_4, c_5$
and order set $O_2$ is made up of items: $c_1, c_2, c_5, c_6, c_7$
then $O_1$ can be described as: $c_3, c_4$ and $S_1=\{c_1, c_2, c_5\}$
and $O_2$ can be described as: $c_6, c_7$ and $S_1$
where $S_1$ is a derived order subset that can be managed independently.

In another embodiment, an order sets group commonality report generated at step 316 of FIG. 3 can help prescribe efficient distribution of order set groups among teams for Content Validation (in step 116 of FIG. 1). Since the report groups order sets based on the set of canonical items common among them, a team getting assigned such a group of order sets rather than a set of random order sets would typically require lesser effort to perform Validation, and all downstream steps of the process.

In another embodiment, an order set pair commonality report can be generated at step 308 to help prioritize work ordering for a team. The report can rank order sets with respect to the number of canonical order items it has common with other order sets in a group. A team validating order sets in order of their ranking can make the most reuse of canonical order items, thereby reducing the overall effort.

In another embodiment, an order set pair commonality report generated at step 308 can compare a raw order set (automatically matched without manual validation) against the Order Set Store to find the most common order set to reuse, based on the percentage coverage. For example, if an existing order set A has a 60% coverage of a raw order set B (e.g., 60% order items in B exist in A), the effort to validate new order items in B would be 40% compared to B's validation without this knowledge. A is identified automatically and referenced for processing of B.

Example

Explaining the Commonality Analysis Process

The following is an example that describes the Commonality Analysis process shown in FIG. 3.

Let us consider steps 412 and 416 in FIG. 4, with order sets A, B, C, D, and E comprising of canonical items $\{c_1, c_2, c_3\}$, $\{c_1, c_2, c_3, c_4, c_5\}$, $\{c_1, c_3, c_6, c_7\}$, $\{c_1, c_4, c_8, c_9, c_{10}\}$, and $\{c_1, c_3, c_8, c_{11}, c_{12}, c_{13}, c_{14}, c_{15}, c_{16}, c_{17}\}$, respectively. We get $$C(A,B)=\{c_1,c_2,c_3\}; p_{ab}=100\% (3/3), p_{ba}=60\%(3/5)$$

$$C(A,C)=\{c_1,c_3\}; p_{ac}=66\%(2/3), p_{ca}=50\%(2/4)$$

$$C(A,D)=\{c_1\}; p_{ad}=33\%(1/3), p_{da}=20\%(1/5)$$

$$C(A,E)=\{c_1,c_3\}; p_{ae}=66\%(2/3), p_{ea}=20\%(2/10)$$

$C(B,C)=\{c_1,c_3\}; p_{bc}=40\%(2/5), p_{cb}=50\%(2/4)$ $C(B,D)=\{c_1,c_4\}; p_{bd}=40\%(2/5), p_{db}=40\%(2/5)$ $C(B,E)=\{c_1,c_3\}; p_{be}=40\%(2/5), p_{eb}=20\%(2/10)$ $C(C,D)=\{c_1\}; p_{cd}=25\%(1/4), p_{dc}=20\%(1/5)$ $C(C,E)=\{c_1,c_3\}; p_{ce}=50\%(2/4), p_{ec}=20\%(2/10)$ $C(D,E)=\{c_1,c_8\}; p_{de}=40\%(2/5), p_{ed}=20\%(2/10)$

Order set A has a total of 8 items common with other order sets, B has 9 items, C has 7 items, D has 6 items, and E has 8 items. Thus, B is ranked top, followed by E, A, C and finally D. Each of A and E has a total of 8 items common with other order sets and each has items common with 4 other order sets but E covers higher percentage of other order sets (66% of A, 50% of C, 40% of B, and 40% of D). In that respect, E is ranked over A.

The order set pair commonality report can also produce a table of order sets ranked in descending order:

TABLE 1

| B | A | C | D | E |
|---|---|---|---|---|
|   | →60% (3/5) | →40% (2/5) | →40% (2/5) | →40% (2/5) |
|   | ←100% (3/3) | ←50% (2/4) | ←40% (2/5) | ←20% (2/10) |
| E | A | C | B | D |
|   | →20% (2/10) | →20% (2/10) | →20% (2/10) | →20% (2/10) |
|   | ←66% (2/3) | ←50% (2/4) | ←40% (2/5) | ←40% (2/5) |
| A | B | C | E | D |
|   | →100% (3/3) | →66% (2/3) | →66% (2/3) | →33% (1/3) |
|   | ←60% (3/5) | ←50% (2/4) | ←20% (2/10) | ←20% (1/5) |
| C | A | B | E | D |
|   | →50% (2/4) | →50% (2/4) | →50% (2/4) | →25% (1/4) |
|   | ←66% (2/3) | ←40% (2/5) | ←20% (2/10) | ←20% (1/5) |
| D | B | E | A | C |
|   | →40% (2/5) | →40% (2/5) | →20% (1/5) | →20% (1/5) |
|   | ←40% (2/5) | ←20% (2/10) | ←33% (1/3) | ←25% (1/4) |

The order set pair commonality report can be used in the following decision making process at step 312 of FIG. 3:

1. Prioritize work order to Reduce Validation and Downstream Process Effort
   a) Validating the order items of order set B first, covers 100% of A, 50% of C, 40% of D, and 20% of E.
   b) Suppose the initial validation of each order item in an order set takes the same amount of time (hypothetically) and let us consider the time required to validate an item is 10 mins. Considering discrete validation of order sets A, B, C, D, and E—A will take 30 mins, B 50 mins, C 40 mins, D 50 mins, and E 100 mins, e.g. 270 mins in total.
   c) Now let us consider the initial validation of the order sets in order of their ranking (in Table-1). Completion of B (50 mins) would leave 0% of A (0 items), 50% of C (2 items), 60% of D (3 items), and 80% of E (8 items) to validate. Validating E (ranked 2) after B further reduces the number of items required to validate (e.g., E has an additional item, $c_8$, common with D).
   d) Validating the order sets in order of B, E, C, A, D would therefore require 50 mins for B, 80 mins for E, 20 mins for C, 0 mins for A, and 20 mins for D, a total of 170 mins.
   e) Reduction in total effort is, therefore, 37%.
2. Reuse of Existing Validated Order Sets
   a) Suppose we have validated set of order sets in the repository (A, C, D, E) and B is a new raw order set requested to validate. Table-1 (in FIG. 8) can help us identify the validated order set (A) in the Order Set Store that has the highest coverage for B. Reusing the common items from A, 60% of B can be covered.

Now let us consider the steps shown in FIG. 5, process 500, with the order sets (A, B, C, D, E) considered above. The steps 508 to 520 generate the Order Set Group Commonality reports with the following order set groups and common item subsets:

TABLE 2

| Rank | Group | Common Subset |
|---|---|---|
| 1 | {A, B, C, E} | $c_1, c_3$ |
| 2 | {A, B} | $c_1, c_2, c_3$ |
| 3 | {A, B, C, D, E} | $c_1$ |
| 4 | {B, D} | $c_4, c_5$ |
| 5 | {D, E} | $c_1, c_8$ |

The reports can be used in the following decision making process at step 312 of FIG. 3.

Organize Order Sets in Hierarchical Structure

Based on the data in Table 2, an order set $G_1=\{c_1, c_3\}$, can be created comprising of items $c_1$ and $c_3$, which can be referenced by order sets A, B, C, E. The order sets can thus be represented as: $A=G_1\cup\{c_2\}$, $B=G_1\cup\{c_2, c_4, c_5\}$, $C=G_1\cup\{c_6, c_7\}$, and $E=G_1\cup\{c_8, c_{11}, c_{12}, c_{13}, c_{14}, c_{15}, c_{16}, c_{17}\}$. Such modularization should facilitate downstream change management.

Optimal Distribution of Work

A team getting order sets that have overlaps with each other should require less time to validate compared to a random distribution.

Figure 6:
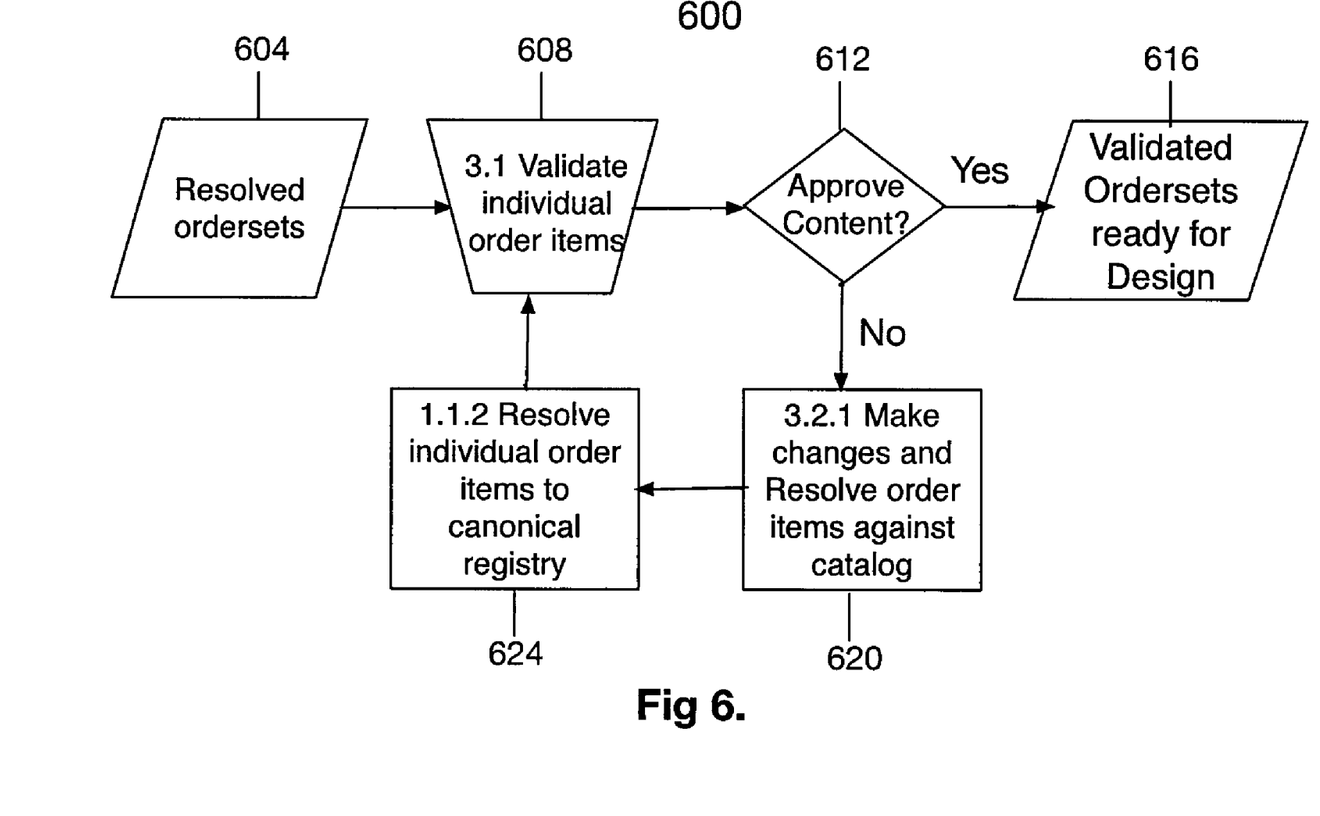
FIG. 6 is a flowchart depicting the Content Validation step of the process of FIG. 1.

Referring to FIG. 6, a flowchart for Order Set Content Validation process 600 is shown. The validation process at step 608 checks all the resolved canonical orders at step 604 within the order sets for clinical appropriateness, evidence support, patient safety, operational policy, and availability of appropriate product or service by the performing departments. The edited Order Set content can then be verified by the authors who initially submitted the corresponding request during a Clinical Review at step 624. The Order Set can be accepted as-is at step 612 or modifications can be recommended or required and proceed to step 620. The process steps can be repeated until the content is ultimately approved by the clinician, or the request cancelled. The process results in a set of validated order sets at step 616.

Figure 7:
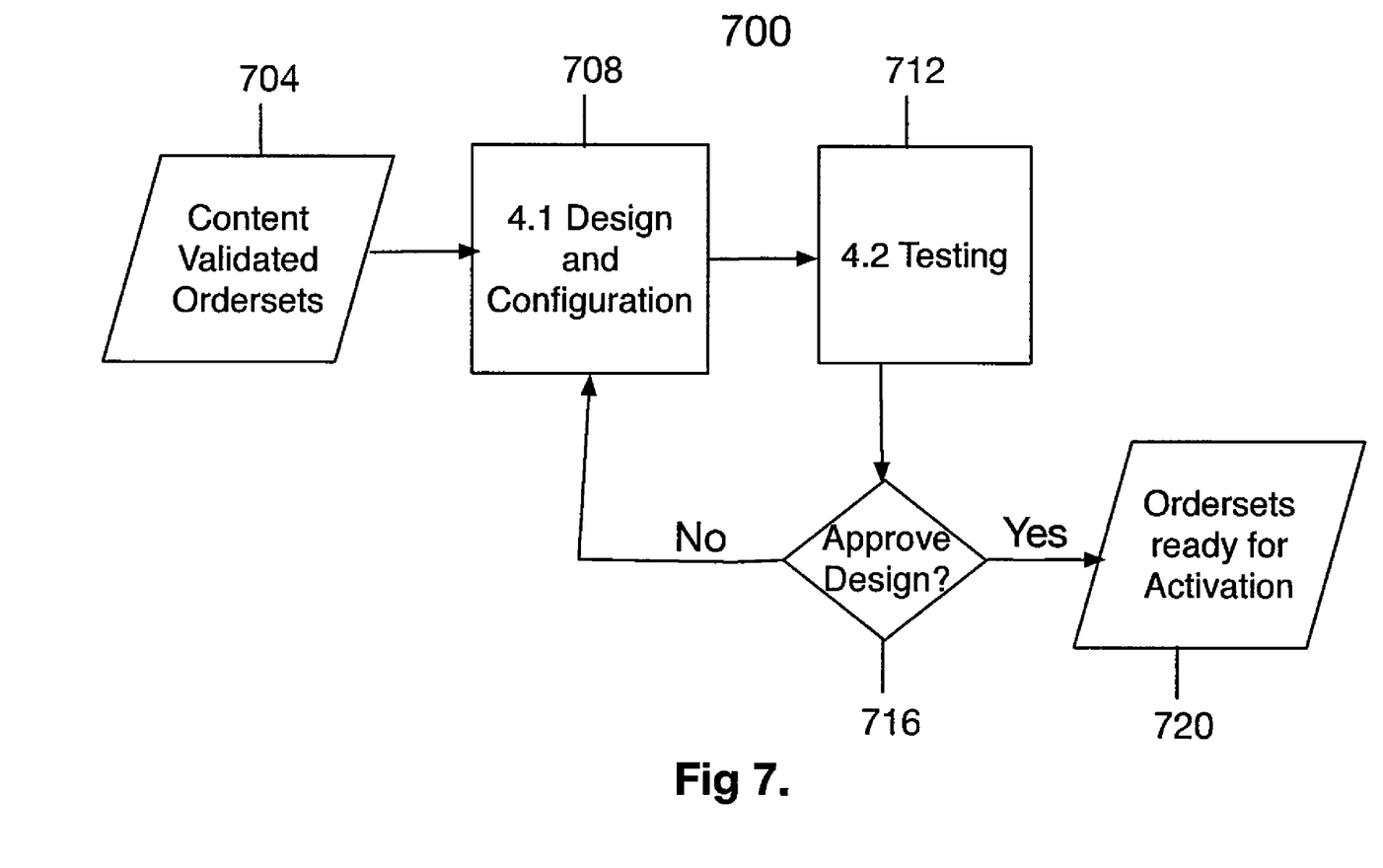
FIG. 7 is a flowchart depicting the Design, Configuration and Testing step of the process of FIG. 1.

Referring to FIG. 7, a flowchart for basic Design, Configuration, and Testing of order sets, process 700, is shown. Once the content is validated at step 704, the order set is transformed into a visual representation for use in a CPOE system. The design steps incorporate clinician preferences, organizational order set design guidelines and CPOE best practices. Once laid out appropriately, an order set design specification or order set configuration can be generated at step 708 for implementing the order set in the CPOE system. Once configured, the order set is tested at step 712 to verify the content in its specification appears in the completed CPOE screens completely and accurately. At step 716, the design can be approved. If not approved, then the process reverts to step 708 for further design and configuration. If approved, then the order set is made ready for activation at step 720.

Figure 8:
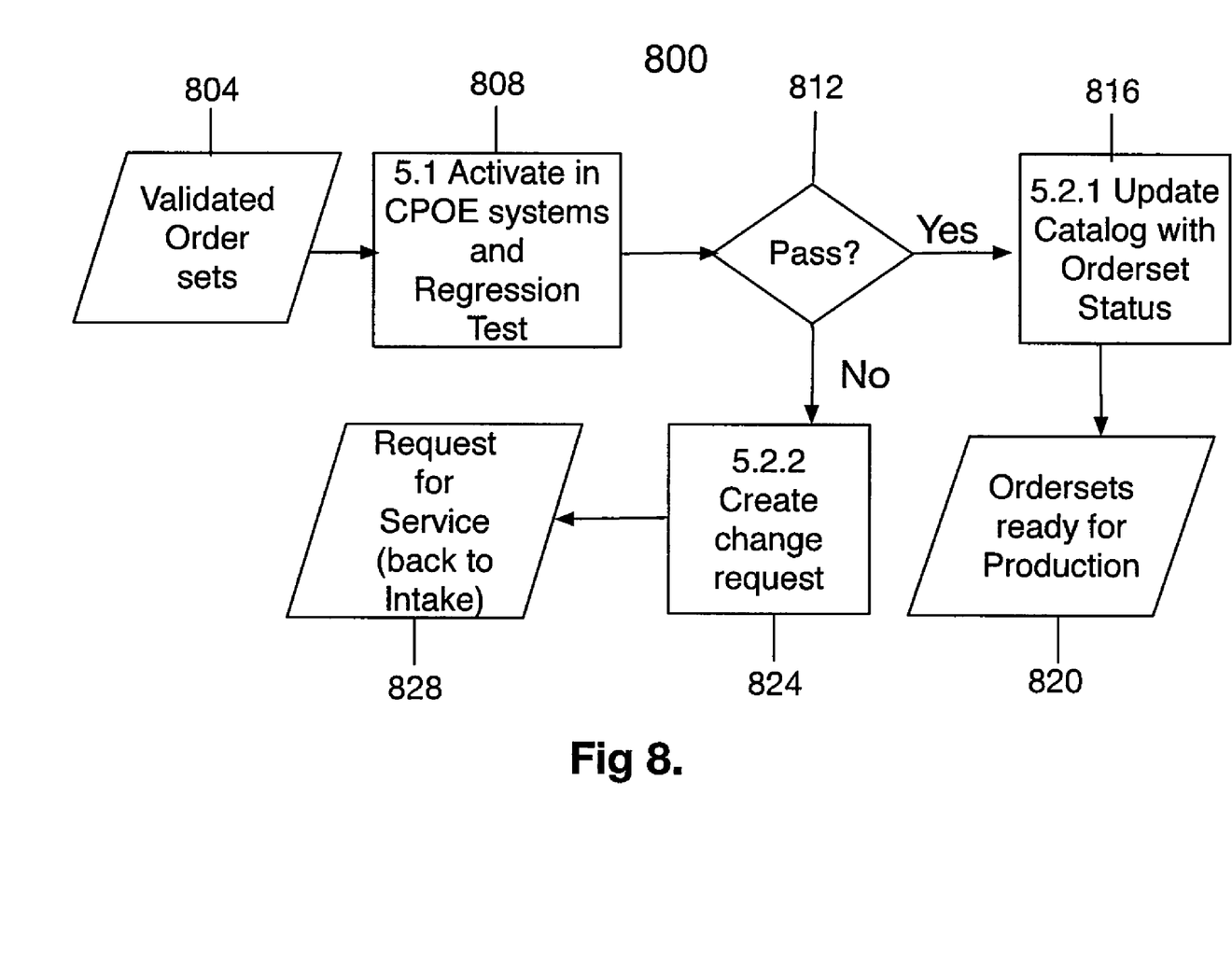
FIG. 8 is a flowchart depicting the Activation step of the process of FIG. 1.

Referring to FIG. 8, a flowchart for basic Activation of Order Sets in a CPOE or EMR system, process 800, is shown. Validated order sets configured and tested at step 804 now are loaded into staging and production systems at step 808. The loads may pass at step 812 if order sets and orderable catalogs in the target CPOE or EMR system are consistent. The loads should fail if order sets and catalog have discrepancies and result in an error. Resolution of errors may result in subsequent change requests either to the order set or the catalog at step 824 and sent back to Intake process 200 at step 828. Once loads succeed, the status of the Order Set is updated to Active at step 816 and made ready for production at step 820.

Figure 9:
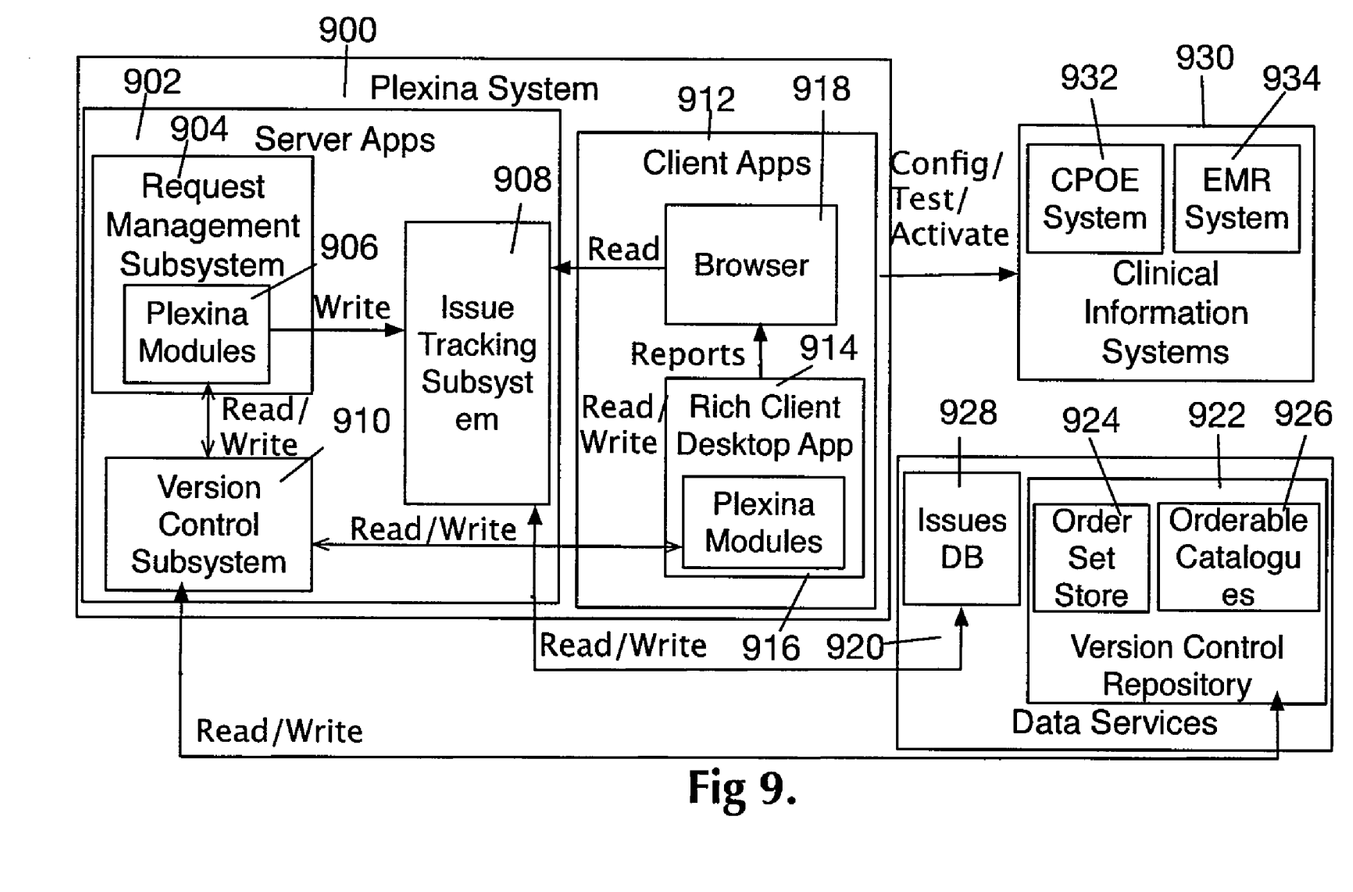
FIG. 9 is a block diagram depicting a system for managing the process of FIG. 1.

Referring to FIG. 9, one embodiment of a system for processing orders and order sets is shown. System 900 can be implemented and operated via an internet website-based application, or via a client workstation or personal computer-based application.

In one embodiment, Server Applications 902 can comprise several general services and subsystems: Request Management Subsystem 904 with Plexina Module 906, embedded Issue Tracking Subsystem 908 and Version Control Subsystem 910. System 900 can further comprise Client Applications 912 including Plexina Analyst 914, a rich-client desktop application, which can also utilize Plexina Module 916. System 900 can further include browser 918 within Client Applications 912 to access Server-based web applications and locally generated reports.

Data Service subsystem 920 can comprise Order Sets 924, Orderable (inventory) Catalogues 926, and Issues database 924 in a combination with Version Control Repository 922.

Plexina Modules 906 and 916 can carry out the steps that incorporate the searching, automated matching, and commonality analysis algorithms as discussed above and shown in FIGS. 3-5, as well as the interaction with data services and domain model abstractions. Plexina Modules 906 and 916 can further produce outputs using any information from the Data Services subsystem 920 in either a server-based or client-based application.

Plexina Client Desktop Application 914 can interact with Plexina Browser 918 to access Issue Tracking Control Subsystem 908 and Version Control Subsystem 910 using standard web based protocols as well known to those skilled in the art including, but not limited to, WEBDAV[1], RSS[2], and XML-RPC[3]. Furthermore, system 900 can communicate with Clinical Information Systems 926 to configure, test and/or activate order sets. Clinical Information Systems 926 can comprise CPOE System 928 and/or EMR System 930.

[1] Web-based Distributed Authoring and Versioning.
[2] Really Simple Syndication.
[3] Extensible Markup Language Remote Procedure Call.

Those skilled in the art will recognize that Plexina Modules 906 and 916 can communicate and interact with both web application services and data services.

It is obvious to those skilled in the art that the methods and processes discussed herein to produce canonical order sets can be used to produce canonical coded clinical documents containing data related to clinical practice guidelines, assessments, measurements, patient charts, population health studies, outcome measurements and clinical objectives, to name but a few examples, that can be compared to other like clinical documents.

It is also obvious to those skilled in the art that the methods and processes discussed herein can be used with electronic patient charts, charts that can be compared to parts of health care plans for compliance analysis both on orders and documentation/data collection. These methods and processes can be used to identify multiple disorders that exhibit similar symptoms, treatment plans and clinical documentation requirements. These methods and process can also be used to determine similarities between other types of clinical intervention standards such as clinical practice guidelines, triage and assessment models, clinical documentation and notes templates as well as disorder related groups.

It is further obvious to those skilled in the art that the methods and processes described herein can be used in the optimization of inventory review processes for the manufacturing of assemblies and products, the assembly of parts, or a recipe of ingredients, etc. Generally, the methods and processes described herein can be used in any process concerning a plurality of parts or items that can be compared item by item.

Although a few embodiments have been shown and described, it will be appreciated by those skilled in the art that various changes and modifications might be made without departing from the scope of the invention. The terms and expressions used in the preceding specification have been used herein as terms of description and not of limitation, and there is no intention in the use of such terms and expressions of excluding equivalents of the features shown and described or portions thereof, it being recognized that the scope of the invention is defined and limited only by the claims that follow.

I claim:

1. A method for implementing raw order sets containing at least one order, the method comprising the steps of:
    a) resolving the at least one raw order set into at least one canonical order set to identify the at least one order within the at least one raw order set; and
    b) performing a commonality analysis by comparing the least one canonical order set with at least one other canonical order set to determine at least one common order subset.

2. The method as set forth in claim 1 further comprising the step of restructuring the at least one canonical order set sharing at least one common order subset into a hierarchical structure.

3. The method as set forth in claim 1 wherein the step of performing the commonality analysis further comprises the step of performing an order set pair commonality analysis.

4. The method as set forth in claim 3 further comprising the steps of:
    a) determining all pairs of order sets;
    b) finding the order set pair percentage coverage and the common canonical items in the order set pairs;
    c) ranking the order set pairs; and
    d) preparing an order-pair commonality report.

5. The method as set forth in claim 1 wherein the step of performing the commonality analysis further comprises the step of performing an order set group commonality analysis.

6. The method as set forth in claim 5 further comprising the steps of:
    a) determining all groups of 2 or more order sets;
    b) finding the common set of canonical items for each order set group;
    c) determining the commonality for each order set group;
    d) ranking the order set groups; and
    e) preparing an order set group commonality report.

7. A method for implementing raw orders containing at least one order item, the method comprising the steps of:
    a) receiving a raw order comprising at least one order item and resolving the at least one order item to a canonical item of an authoritative catalogue of order items to produce a canonical order set;
    b) performing a commonality analysis on the canonical order set by comparing the canonical order set to other canonical order sets and organizing the canonical order set into a hierarchical structure or a prioritized order;
    c) validating the at least one order item in the canonical order set to produce a validated order set;
    d) configuring and testing the validated order set; and
    e) activating the validated order set.

8. The method as set forth in claim 7 wherein the step of receiving a raw order set further comprises the step of creating an order set work document for a request for a new order set.

9. The method as set forth in claim 7 wherein the step of receiving a raw order set further comprises the step of looking up relevant order sets in an order set store for a request for changes to an existing order set.

10. The method as set forth in claim 7 wherein the step of performing the commonality analysis further comprises the step of performing an order set pair commonality analysis.

11. The method as set forth in claim 10 further comprising the steps of:
 a) determining all pairs of order sets;
 b) finding the order set pair percentage coverage and the common canonical items in the order set pairs;
 c) ranking the order set pairs; and
 d) preparing an order-pair commonality report.

12. The method as set forth in claim 7 wherein the step of performing the commonality analysis further comprises the step of performing an order set group commonality analysis.

13. The method as set forth in claim 12 further comprising the steps of:
 a) determining all groups of 2 or more order sets;
 b) finding the common set of canonical items for each order set group;
 c) determining the commonality for each order set group;
 d) ranking the order set groups; and
 e) preparing an order set group commonality report.

14. The method as set forth in claim 7 wherein the step of validating the at least one order item further comprises the step of approving the content of the at least one order item or making changes to the at least one order item.

15. The method as set forth in claim 7 wherein the step of configuring and testing the validated order set further comprises the step of approving the design of the validated order set.

16. The method as set forth in claim 15 further comprising the step of re-designing or re-configuring the validated order set if the design of the validated order set is not approved.

17. The method as set forth in claim 7 further comprising the step of activating the validated order set in a computerized provider order entry system.

18. The method as set forth in claim 17 further comprising the step of determining whether the validated order set and order items in an order set catalogue are consistent.

19. The method as set forth in claim 18 further comprising the step of creating a change request to the validated order set if the validated order set is not consistent with the order set catalogues.

20. A system for implementing raw order sets containing at least one order, the system comprising a general purpose computing platform having a processor and a non-transitory computer-readable storage medium and a computer executable program stored in the computer-readable storage medium, wherein when the computer executable program is executed by the processor, the general purpose computing platform comprises:
 a) means for resolving the at least one raw order set into at least one canonical order set to identify the at least one order within the at least one raw order set; and
 b) means for performing a commonality analysis by comparing the one canonical order set with at least one other canonical order set to determine at least one common order subset.

21. The system as set forth in claim 20 further comprising means for prioritizing the restructuring of the at least one canonical order set sharing at least one common order subset into a hierarchical structure.

22. The system as set forth in claim 20 further comprising means for performing an order set pair commonality analysis.

23. The system as set forth in claim 22 further comprising:
 a) means for determining all pairs of order sets;
 b) means for finding the order set pair percentage coverage and the common canonical items in the order set pairs;
 c) means for ranking the order set pairs; and
 d) means for preparing an order-pair commonality report.

24. The system as set forth in claim 20 further comprising means for performing an order set group commonality analysis.

25. The system as set forth in claim 24 further comprising:
 a) means for determining all groups of 2 or more order sets;
 b) means for finding the common set of canonical items for each order set group;
 c) means for determining the commonality for each order set group;
 d) means for ranking the order set groups; and
 e) means for preparing an order set group commonality report.

26. A system for implementing raw orders containing at least one order item, the system comprising a general purpose computing platform having a processor and a non-transitory computer-readable storage medium and a computer executable program stored in the computer-readable storage medium, wherein when the computer executable program is executed by the processor, the general purpose computing platform comprises:
 a) means for receiving a raw order comprising at least one order item and resolving the at least one order item to a canonical item of an authoritative catalogue of order items to produce a canonical order set;
 b) means for performing a commonality analysis on the canonical order set by comparing the canonical order set to other canonical order sets and organizing the canonical order set into a hierarchical structure or a prioritized order;
 c) means for validating the at least one order item in the canonical order set to produce a validated order set;
 d) means for configuring and testing the validated order set; and
 e) means for activating the validated order set.

27. A method for implementing raw order sets containing at least one order, the method being embodied on a non-transitory computer-readable storage medium such that, when implemented on a general purpose computing platform, the method permits the implementation of a raw order set containing at least one order, the non-transitory computer-readable storage medium comprising:
 a) a software code segment that resolves the at least one raw order set into at least one canonical order set to identify the at least one order within the at least one raw order set; and
 b) a software code segment that performs a commonality analysis by comparing the one canonical order set with at least one other canonical order set to determine at least one common order subset.

28. The method as set forth in claim 27 wherein the non-transitory computer-readable storage medium further comprises a software code segment that prioritizes the restructuring of the at least one canonical order set sharing at least one common order subset into a hierarchical structure.

29. A method for implementing raw orders containing at least one order item, the method being embodied on a non-transitory computer-readable storage medium such that, when implemented on a general purpose computing platform, the method permits the implementation of raw orders containing at least one order item, the non-transitory computer-readable storage medium comprising:
  a) a software code segment that receives a raw order comprising at least one order item and resolving the at least one order item to a canonical item of an authoritative catalogue of order items to produce a canonical order set; and
  b) a software code segment that performs a commonality analysis on the canonical order set by comparing the canonical order set to other canonical order sets and organizing the canonical order set into a hierarchical structure or a prioritized order.

30. The method as set forth in claim 29 further comprising a software code segment that validates the at least order item in the canonical order set to produce a validated order set.

31. The method as set forth in claim 30 further comprising a software code segment that configures and tests the validated order set.

32. The method as set forth in claim 31 further comprising a software code segment that activates the validated order set.

* * * * *